US011445897B2

(12) United States Patent
Yashiro et al.

(10) Patent No.: US 11,445,897 B2
(45) Date of Patent: Sep. 20, 2022

(54) ENDOSCOPE WITH HOLDING MEMBER HAVING MULTIPLE INDEPENDENT WALL PARTS

(71) Applicant: FUJIFILM Corporation, Tokyo (JP)

(72) Inventors: Takashi Yashiro, Kanagawa (JP); Issei Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 697 days.

(21) Appl. No.: 16/384,947

(22) Filed: Apr. 16, 2019

(65) Prior Publication Data

US 2019/0239733 A1    Aug. 8, 2019

Related U.S. Application Data

(63) Continuation of application No. PCT/JP2017/031774, filed on Sep. 4, 2017.

(30) Foreign Application Priority Data

Oct. 25, 2016  (JP) .............................. JP2016-209056

(51) Int. Cl.
| A61B 1/05 | (2006.01) |
| G02B 23/24 | (2006.01) |
| H04N 5/225 | (2006.01) |
| A61B 1/045 | (2006.01) |
| G02B 23/26 | (2006.01) |

(Continued)

(52) U.S. Cl.
CPC ................. *A61B 1/05* (2013.01); *A61B 1/00* (2013.01); *A61B 1/04* (2013.01); *A61B 1/045* (2013.01);

(Continued)

(58) Field of Classification Search
None
See application file for complete search history.

(56) References Cited

U.S. PATENT DOCUMENTS

| 6,547,721 B1* | 4/2003 | Higuma ................. A61B 1/051 600/133 |
| 2005/0179805 A1* | 8/2005 | Avron ............... H01L 27/14625 348/340 |

(Continued)

FOREIGN PATENT DOCUMENTS

| JP | 2015062555 | 4/2015 |
| JP | 2015073540 | 4/2015 |
| WO | 2016042804 | 3/2016 |

OTHER PUBLICATIONS

"International Search Report (Form PCT/ISA/210) of PCT/JP2017/031774," dated Nov. 14, 2017, with English translation thereof, pp. 1-5.

(Continued)

*Primary Examiner* — John P Leubecker
(74) *Attorney, Agent, or Firm* — JCIPRNET

(57) ABSTRACT

An endoscope includes an image pick-up-device at a distal-end-part of an insertion-part. The image pick-up-device includes a lens barrel holding an imaging lens; an image-sensor having a rectangular shape as an outer peripheral shape of an image reception surface on which imaging light incident via the imaging lens; and a sensor holder holding the image-sensor in a state where the image reception surface intersects a longitudinal direction of the insertion-part. The sensor holder has three independent wall-parts respectively covering three side surfaces of the image-sensor, and on an XY plane orthogonal to the longitudinal direction of the insertion-part, a gap length, in an X-axis direction on the plane between adjacent wall-parts of the three wall-parts and a gap length, in Y-axis direction, between the adjacent wall-parts are equal to each other. Additionally, the height of each of the three wall-parts is 1.5 times to 3 times the gap length.

18 Claims, 13 Drawing Sheets

(51) Int. Cl.
*A61B 1/04* (2006.01)
*A61B 1/00* (2006.01)

(52) U.S. Cl.
CPC ......... *G02B 23/2484* (2013.01); *G02B 23/26* (2013.01); *H04N 5/2253* (2013.01); *H04N 5/2254* (2013.01); *A61B 1/00096* (2013.01); *H04N 2005/2255* (2013.01)

(56) References Cited

U.S. PATENT DOCUMENTS

| | | | |
|---|---|---|---|
| 2013/0172674 A1* | 7/2013 | Kennedy, II | ....... A61B 1/00195 600/109 |
| 2013/0172678 A1* | 7/2013 | Kennedy, II | ......... A61B 1/0011 600/112 |
| 2014/0336457 A1 | 11/2014 | Kuhn et al. | |
| 2015/0062316 A1* | 3/2015 | Haraguchi | ......... A61B 1/00009 348/65 |
| 2015/0312457 A1 | 10/2015 | Kojima | |
| 2017/0035279 A1* | 2/2017 | Fujii | ...................... A61B 1/051 |
| 2017/0064249 A1* | 3/2017 | Kitano | ................. H04N 5/2253 |
| 2017/0269349 A1* | 9/2017 | Usuda | .................... A61B 1/051 |

OTHER PUBLICATIONS

"Written Opinion of the International Searching Authority (Form PCT/ISA/237) of PCT/JP2017/031774," dated Nov. 14, 2017, with English translation thereof, pp. 1-7.

\* cited by examiner

ENDOSCOPE WITH HOLDING MEMBER HAVING MULTIPLE INDEPENDENT WALL PARTS

CROSS-REFERENCE TO RELATED APPLICATIONS

This application is a Continuation of PCT International Application No. PCT/JP2017/031774 filed on Sep. 4, 2017, which claims priority under 35 U.S.C. § 119(a) to Japanese Patent Application No. 2016-209056 filed on Oct. 25, 2016. Each of the above application(s) is hereby expressly incorporated by reference, in its entirety, into the present application.

BACKGROUND OF THE INVENTION

1. Field of the Invention

The present invention relates to an endoscope.

2. Description of the Related Art

Image pick-up devices of endoscopes comprise a solid-state image pick-up element, a lens barrel that holds an imaging lens for forming an optical image on an image reception surface of the solid-state image pick-up element, and a sensor holder that couples the solid-state image pick-up element and the lens barrel to each other. The sensor holder is an important holding member that holds the solid-state image pick-up element and the lens barrel in a state where a focal point and an optical axis of the imaging lens held by the lens barrel are adjusted in conformity of the image reception surface of the solid-state image pick-up element. An endoscope of JP2015-073540A also comprises a tubular lens barrel in which a lens for imaging incident light is housed, an optical member holder comprising a barrel hole that houses the lens barrel, and an image pick-up element mounted so as to block one end of the optical member holder.

SUMMARY OF THE INVENTION

The solid-state image pick-up element to be used for the image pick-up devices of the endoscopes is very small-sized in order to reduce the diameter of the image pick-up devices, and the size of the image reception surface is about 1 mm$^2$. Not only the solid-state image pick-up element, but also the lens barrel and the sensor holder to be used are small-sized in a radial direction in order to reduce the diameter of the image pick-up devices. For this reason, machining of complicated structures by a machining tool has high difficulty, and small-sized components with high shape accuracy cannot be manufactured unless these components have simple structure suitable for the size of the machining tool.

The invention has been made in view of the above-described circumstances, and an object thereof is to provide an endoscope comprising an image pick-up device having high easiness of machining by a machining tool and excellent manufacturability.

An endoscope of one aspect of the invention comprises an image pick-up device at a distal end part of an insertion part capable of being inserted into a body cavity. The image pick-up device includes a housing member that holds an imaging lens; a solid-state image pick-up element that photoelectrically converts imaging light incident on an image reception surface via the imaging lens and has a rectangular shape as an outer peripheral shape of the image reception surface; and a holding member that holds the solid-state image pick-up element in a state where the image reception surface intersects a longitudinal direction of the insertion part. The holding member has three independent wall parts that respectively cover three of four side surfaces that constitute an outer peripheral surface of the solid-state image pick-up element. On a plane orthogonal to the longitudinal direction of the insertion part, A gap length, in a first direction on the plane, between adjacent wall parts of the three wall parts and a gap length, in a second direction perpendicular to the first direction on the plane, between the adjacent wall parts are equal to each other, and a height of the three wall parts is 1.5 times to 3 times the gap length.

Although a machining tool in which the external diameter of the machining tool that forms a gap between the three wall parts is equal to the gap length between the adjacent wall parts of the three wall parts and the cutting edge length of the machining tool is equal to or greater than the height of the wall parts is used, there is a possibility that the machining tool is distorted during machining in a case where the cutting edge length is longer than the external diameter of the machining tool. According to the invention, since the height of the three wall parts is 1.5 times to 3 times the gap length between the adjacent wall parts, the machining tool of the cutting edge length that is 1.5 times to 3 times the external diameter is used. For this reason, easiness of machining by the machining tool can be increased while guaranteeing the shape accuracy of the wall parts, the gap, and the like. Hence, the image pick-up device comprising the holding member with high manufacturability can be manufactured.

DESCRIPTION OF THE PREFERRED EMBODIMENTS

Hereinafter, embodiments of the invention will be described with reference to the drawings.

Figure 1:
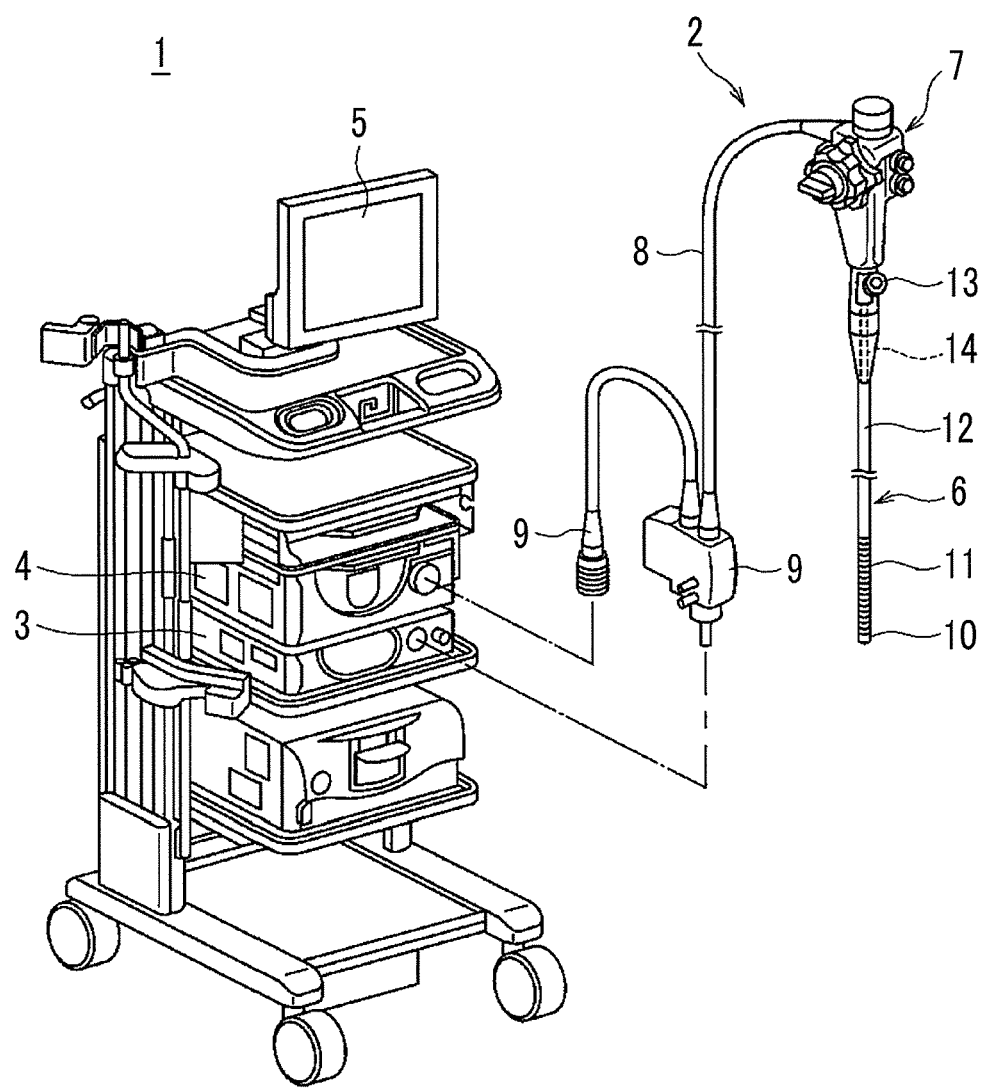
FIG. 1 is a perspective view illustrating an example of an endoscope system for explaining an embodiment of the invention.

FIG. 1 is a perspective view illustrating an example of an endoscope system for explaining an embodiment of the invention.

An endoscope system 1 comprises an endoscope 2, a light source unit 3, and a processor unit 4. The endoscope 2 has an insertion part 6 capable of being inserted into a body cavity of a subject, an operating part 7 connected to the insertion part 6, and a universal cord 8 extending from the operating part 7, the insertion part 6 is provided on a distal end side of the endoscope 2, and the universal cord 8 is provided on a proximal end side of the endoscope 2. The insertion part 6 is constituted of a distal end part 10, a bending part 11 connected to the distal end part 10, and a flexible part 12 that connects the bending part 11 and the operating part 7 together, the distal end part 10 is provided on a distal end side in a longitudinal axis of the insertion part 6, and the flexible part 12 is provided on a proximal end side in the longitudinal axis. In addition, the distal end side in the longitudinal axis of the insertion part 6 is the same as the distal end side of the endoscope 2, and the proximal end side in the longitudinal axis of the insertion part 6 is the same as the proximal end side of the endoscope 2.

The distal end part 10 is provided with an illumination optical system that emits illumination light for illuminating an observation region, an image pick-up device and an image pick-up optical system that picks up an image of an observation region, and the like. The bending part 11 is configured to be bendable in a direction orthogonal to the longitudinal axis of the insertion part 6, and the bending operation of the bending part 11 is operated in the operating part 7. Additionally, the flexible part 12 is configured to be relatively flexible so as to be deformable along the shape of an insertion path of the insertion part 6.

The operating part 7 is provided with a button that operates an image pick-up operation of the image pick-up device of the distal end part 10, a knob that operates the bending operation of the bending part 11, and the like. Additionally, the operating part 7 is provided with an introduction port 13 into which a treatment tool, such as an electric scalpel, are introduced, and a treatment tool channel 14 which reaches the distal end part 10 from the introduction port 13 and through which a treatment tool is inserted is provided inside the insertion part 6.

A terminal of the universal cord 8 is provided with a connector 9, and the endoscope 2 is connected via the connector 9 to the light source unit 3 that generates the illumination light emitted from the illumination optical system of the distal end part 10, and the processor unit 4 that processes video signals acquired by the image pick-up device of the distal end part 10. The processor unit 4 processes the input video signals to generate video data of the observation region, and displays and records the generated video data on a monitor 5.

A light guide and an electric wire group are housed inside the insertion part 6, the operating part 7, and the universal cord 8. The illumination light generated in the light source unit 3 is guided to the illumination optical system of the distal end part 10 via the light guide, and signals and electrical power are transmitted via the electric wire group between the image pick-up device of the distal end part 10 and the processor unit 4.

Figure 2:
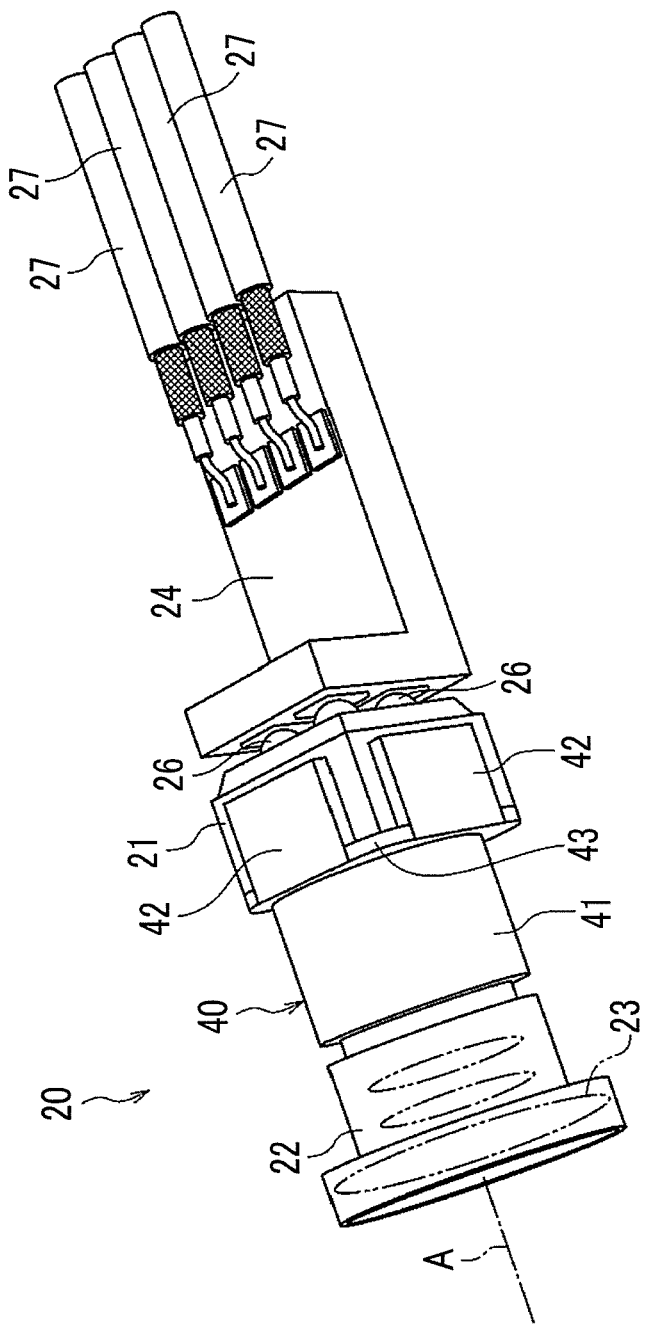
FIG. 2 is a perspective view illustrating an internal configuration of an image pick-up device loaded on a distal end part of an insertion part of the endoscope system illustrated in FIG. 1.

FIG. 2 is a perspective view illustrating an internal configuration of an image pick-up device 20 loaded on the distal end part 10 of the insertion part 6.

The image pick-up device 20 comprises an image sensor (solid-state image pick-up element) 21, a lens barrel (housing member) 22 that housed an imaging lens 23, and a sensor holder (holding member) 40 that holds the image sensor 21. In addition, the lens barrel 22 is fitted to the sensor holder 40. Additionally, the image sensor 21 is mounted on a circuit board 24 and is connected to the processor unit 4 via the circuit board 24 and transmission cables 27.

Hereinafter, respective constituent elements provided in the image pick-up device 20 will be described.

The image sensor 21 is a solid-state image pick-up element, such as a charge coupled device (CCD) type image sensor or a complementary metal oxide semiconductor (CMOS) image sensor, and photoelectrically converts an optical image formed on an image reception surface. The shape of the image sensor 21 as seen from the image reception surface side is substantially square, and the external diameter of the image sensor 21 as seen in a normal direction of the image reception surface is equal to or less than 1 mm$^2$. A plurality of connecting terminals 26 which signals and electrical power are input to and output from are provided on a back surface opposite to the image reception surface of the image sensor 21.

The lens barrel 22 houses at least one imaging lens 23 that forms a subject image on the image reception surface of the image sensor 21.

The sensor holder 40 holds the image sensor 21 on a proximal end side thereof, and holds the lens barrel 22 on a distal end side thereof. In addition, the image sensor 21 is held by the sensor holder 40 in a state where the image reception surface intersects a longitudinal direction of the insertion part 6, and the lens barrel 22 is held by being fitted to the sensor holder 40. The lens barrel 22 fitted to the sensor holder 40 is movable along an optical axis A of the imaging lens 23, and the position of the imaging lens 23 with respect to the image sensor 21 can be adjusted by moving the lens barrel 22.

Figure 3:
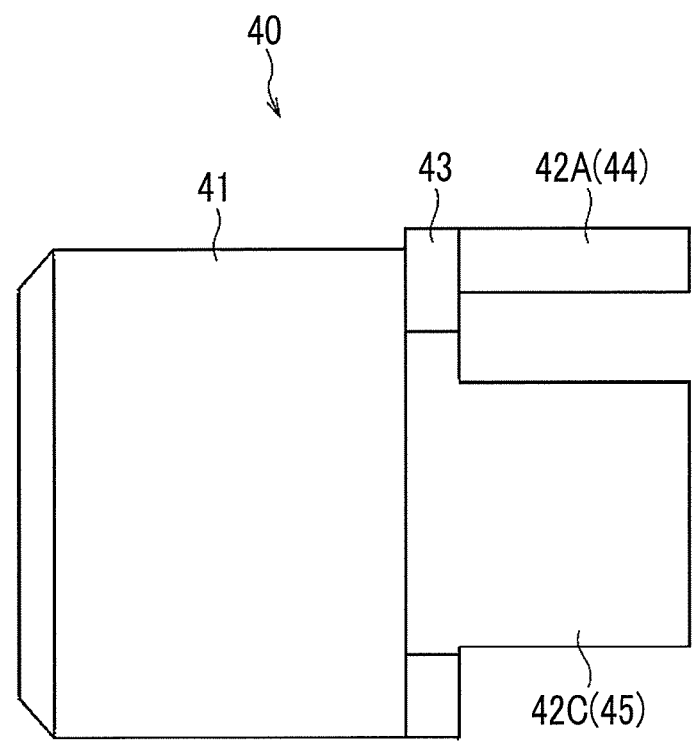
FIG. 3 is a side view of a sensor holder of the image pick-up device illustrated in FIG. 2.
Figure 4:
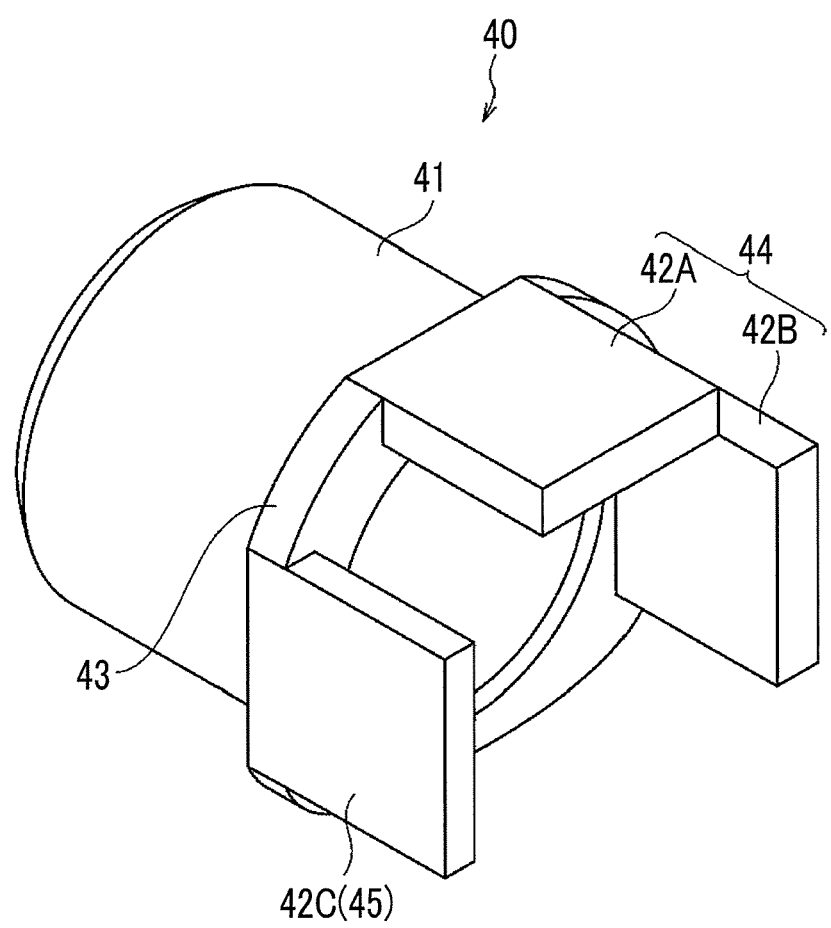
FIG. 4 is a perspective view of a proximal end side of the sensor holder of the image pick-up device illustrated in FIG. 2.
Figure 5:
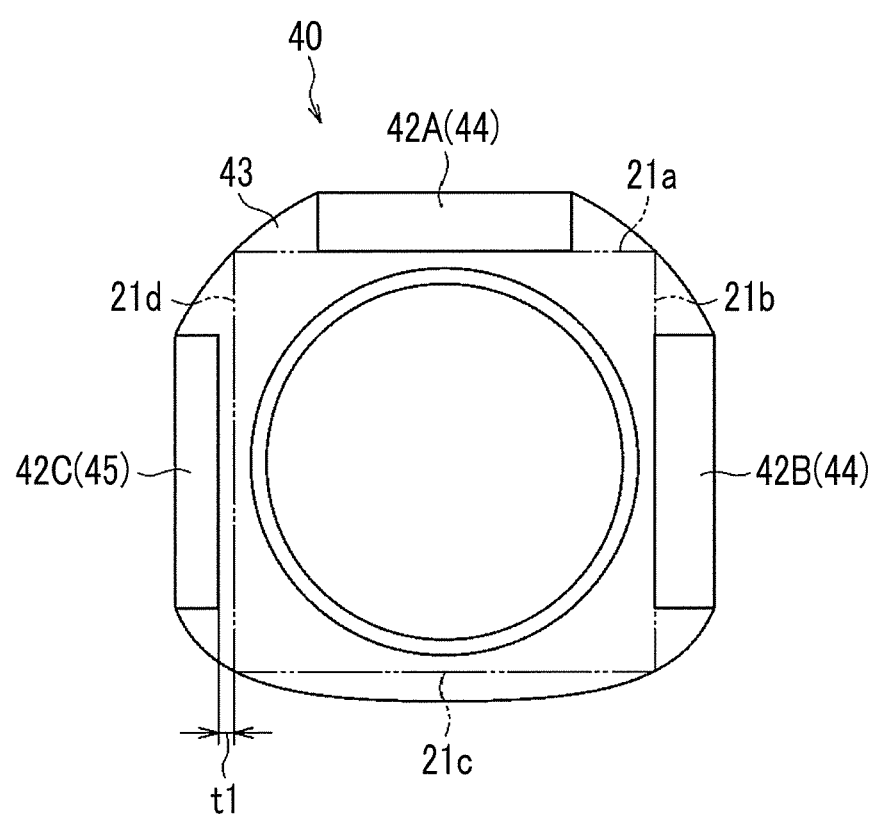
FIG. 5 is a back view of the sensor holder as seen from the proximal end side of the image pick-up device illustrated in FIG. 2.

Hereinafter, the details of the structure of the sensor holder 40 will be described with reference to FIGS. 3 to 5. FIG. 3 is a side view of the sensor holder 40. FIG. 4 is a perspective view of the proximal end side of the sensor holder 40. FIG. 5 is a front view of the sensor holder 40 as seen from the proximal end side.

The sensor holder 40 has a cylindrical fitting part 41 to be fitted to the lens barrel 22, and an extending wall part 42 that extends in the longitudinal direction of the insertion part 6 from the fitting part 41 to cover at least a portion of an outer peripheral surface of the image sensor 21. The extending wall part 42 is configured integrally with the fitting part 41 via a flange part 43. Additionally, the extending wall part 42 includes three independent wall parts 42A, 42B, and 42C that respectively cover three of four side surfaces that constitute the outer peripheral surface of the image sensor 21.

Two wall parts 42A and 42B, which are orthogonal to each other, among the three wall parts 42A, 42B, and 42C constitute a first wall portion 44 for causing two side surfaces 21a and 21b, which are orthogonal to each other, among four side surfaces 21a to 21d that constitute the outer peripheral surface of the image sensor 21, to abut against each other to position the image sensor 21 with respect to the sensor holder 40. Additionally, the wall part 42C, which faces a wall part (wall part 42B) that constitutes the first wall portion 44, constitute a second wall portion 45 that faces one side surface 21d of the four side surfaces 21a to 21d of the image sensor 21. A gap of a size t1 is present between the image sensor 21 abutting against the first wall portion 44 and the second wall portion 45. In addition, the size t1 of the gap is preferably 0.1 mm or less.

Figure 6:
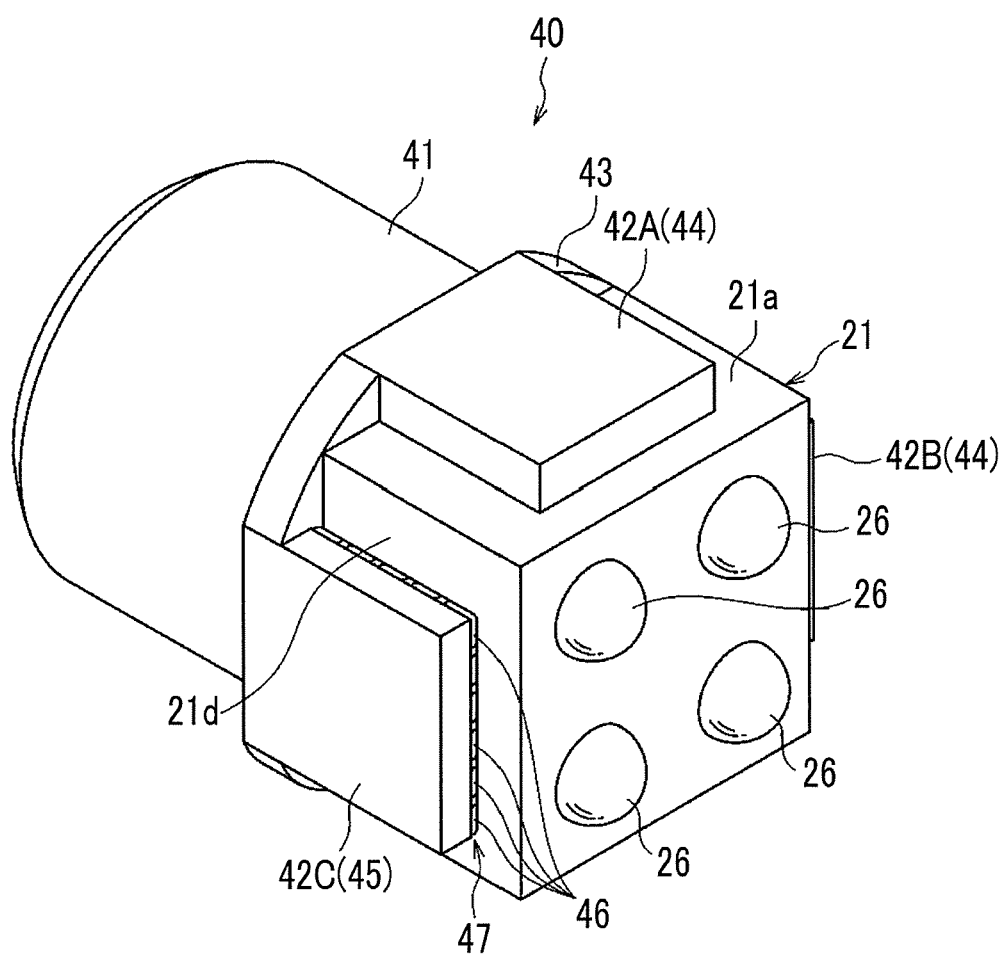
FIG. 6 is a perspective view of the proximal end side illustrating a state where an image sensor is held by the sensor holder.

FIG. 6 is a perspective view of the proximal end side illustrating a state where the image sensor 21 is held by the sensor holder 40. An adhesive layer 47 is formed by filling the gap, which is present between the image sensor 21 and the second wall portion 45, with an adhesive 46 in a state where the first wall portion 44 is positioned in abutment with the image sensor 21, and the image sensor 21 is fixed to the second wall portion 45. In addition, the adhesive 46 may be an ultraviolet curable adhesive or may be an instant adhesive.

Figure 7:
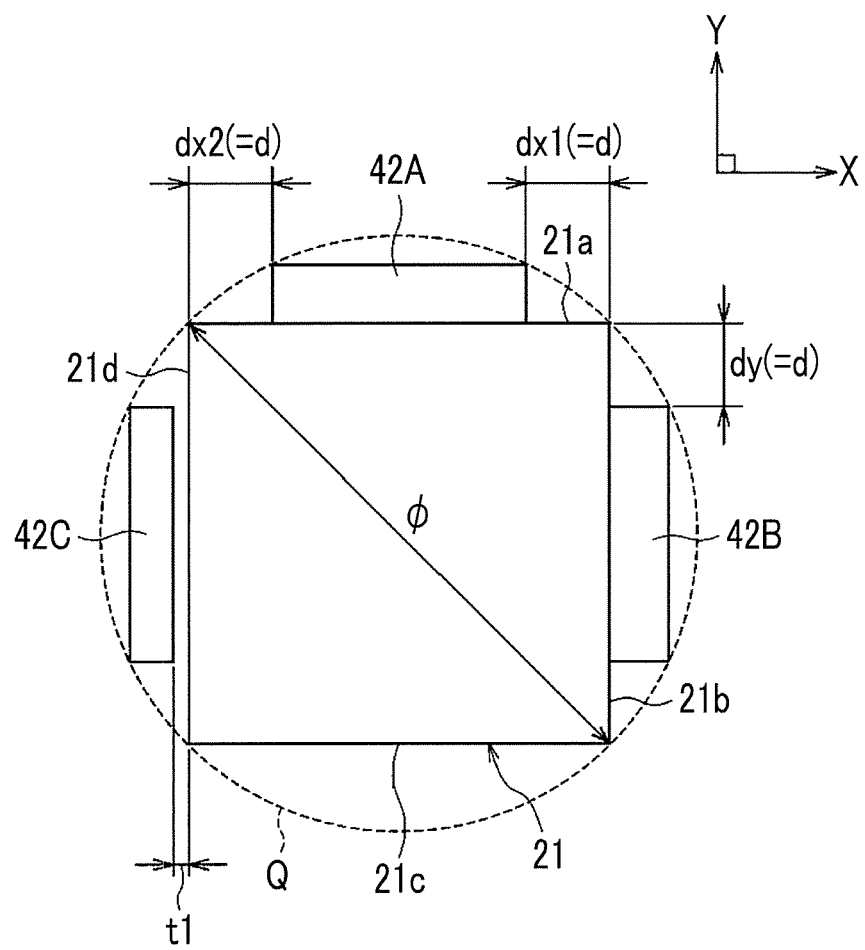
FIG. 7 is a conceptual diagram illustrating a positional relationship of three wall parts in a case where the sensor holder holding the image sensor is seen from the proximal end side.

FIG. 7 is a conceptual diagram illustrating a positional relationship of the three wall parts 42A, 42B, and 42C in a case where the sensor holder 40 holding the image sensor 21 is seen from the proximal end side. The three wall parts 42A, 42B, and 42C of the sensor holder 40 are located inside a circumscribed circle Q of the image sensor 21 in a case where the sensor holder 40 is seen in the longitudinal direction of the insertion part 6. The circumscribed circle Q is a circle that has a length $\phi$ of a diagonal line of the rectangular image sensor 21 as a diameter. In other words, four peaks that constitute an outer periphery of the image sensor 21 are inscribed on the circumscribed circle Q.

Since the three wall parts 42A, 42B, and 42C are located inside the circumscribed circle Q, the respective wall parts are respectively independent via the gap. Hereinafter, the gap between the wall parts will be described. A gap length, in a first direction (X-axis direction), of between adjacent wall parts of the three wall parts 42A, 42B, and 42C on a plane (XY plane) orthogonal to the longitudinal direction in a case where the sensor holder 40 is seen in the longitudinal direction of the insertion part 6, and a gap length in a second direction (Y-axis direction) orthogonal to the first direction on the above plane are all equal. That is, a gap dx1 between the wall part 42A and the wall part 42B and a gap dx2 between the wall part 42A and the wall part 42C, in the X-axis direction on the XY plane illustrated in FIG. 7, and a gap dy between the wall part 42A and the wall part 42B or between the wall part 42A and the wall part 42C in the Y-axis direction are all equal, and a relational expression of dx1=dx2=dy=d is established.

Additionally, since the three wall parts 42A, 42B, and 42C are located inside the circumscribed circle Q, the wall part 42C having the gap of the size t1 between the wall part 42C and the image sensor 21 is thinner than the wall parts 42A and 42B by the size t1 of the above gap.

Figure 8:
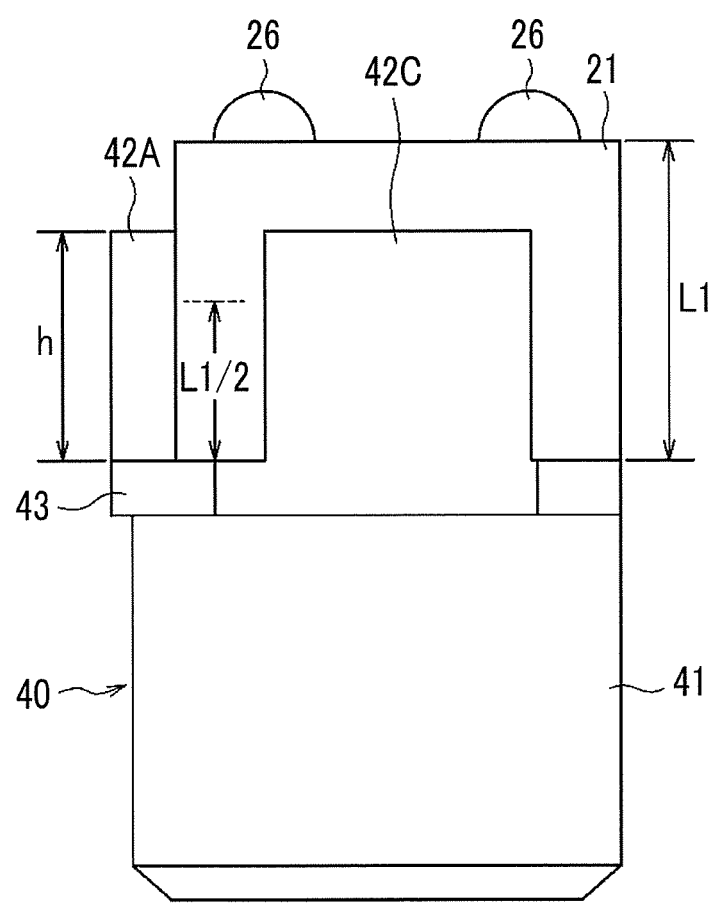
FIG. 8 is a view illustrating a relationship of the height of the wall parts of the sensor holder over the image sensor held by the sensor holder.
Figure 9:
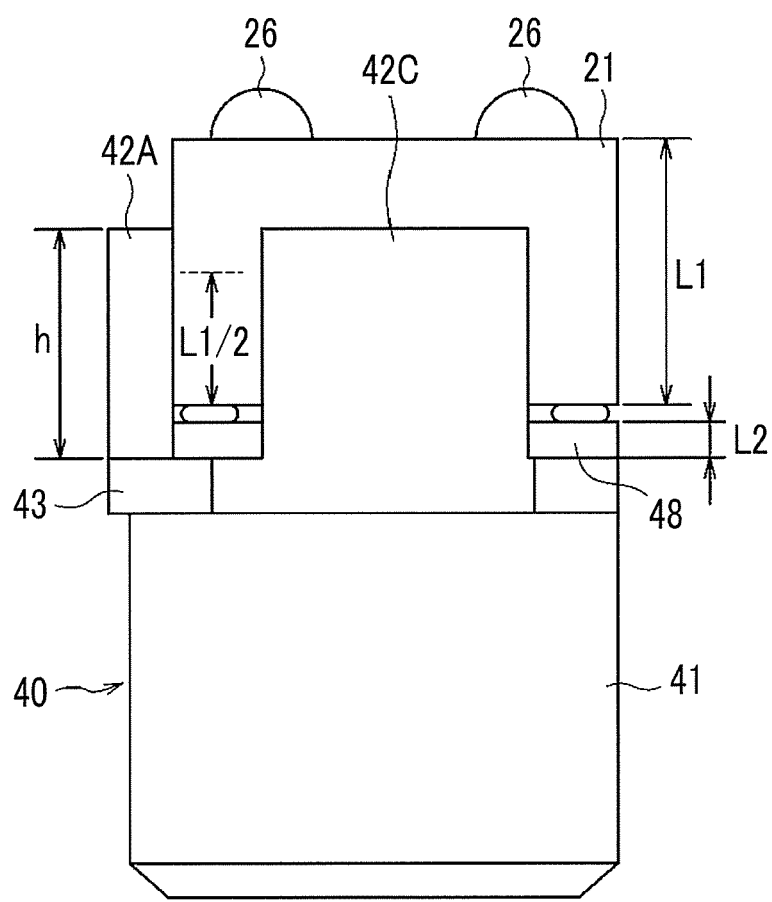
FIG. 9 is a view illustrating a relationship of the height of the wall parts of the sensor holder over the image sensor held by the sensor holder.

Next, the height of the three wall parts 42A, 42B, and 42C of the sensor holder 40 will be described. FIGS. 8 and 9 are views illustrating a relationship of the height of the wall part 42C of the sensor holder 40 with respect to the image sensor 21 held by the sensor holder 40. In addition, in an example illustrated in FIG. 9, a cover glass 48 is provided on the image reception surface of the image sensor 21. In addition, the height of each wall part indicates the length of a wall part extending from the flange part 43.

In an example illustrated in FIG. 8, a height h of the wall parts 42A, 42B, and 42C is less than a thickness L1 of the image sensor 21 excluding the height of the connecting terminals 26 and is equal to or greater than half (=L1/2) of the thickness L1. Additionally, as illustrated in FIG. 9, in a case where the cover glass 48 is provided on the image reception surface of the image sensor 21, the height h of the wall parts 42A, 42B, and 42C is less than a sum (=L1+L2) of the thickness L1 of the image sensor 21 and a thickness L2 of the cover glass 48 excluding the height of the connecting terminals 26 and is equal to or greater than a sum (=L1/2+L2) of half of the thickness L1 and the thickness L2. In addition, a gap for bonding the cover glass 48 to the image sensor 21 illustrated in FIG. 9 is very thin with respect to the thicknesses L1 and L2.

In addition, in either case of FIGS. 8 and 9, the height h of the wall parts 42A, 42B, and 42C is selected to be in a range of 1.5 times to 3 times the gap length d between the adjacent wall parts illustrated in FIG. 7. That is, a relational expression of 1.5d≤h≤3d is established.

The three wall parts 42A, 42B, and 42C of the sensor holder 40 having the configuration described above are formed by performing cutting work with an end mill of an external diameter equal to the above gap length d. Since the end mill may be moved along an X-axis or Y-axis on the XY plane illustrated in FIG. 7 during the cutting work, the gap between the adjacent wall parts of the three wall parts 42A, 42B, and 42C can be easily formed. Additionally, by using the end mill of a cutting edge length longer than the height h, the three wall parts 42A, 42B, and 42C of the height h extending from the fitting part 41 via the flange part 43 can be easily formed. In addition, in the gap length d between the wall parts formed by the cutting work using the end mill, an error of about 5% is included in the respective gaps dx1, dx2, and dy due to shake or vibration of the end mill on the XY plane illustrated in FIG. 7 that may occur during the cutting work. That is, "the respective gaps dx1, dx2, and dy are all equal" means that mutual differences are considered to be equal in a case where the mutual differences are respectively less than 10%.

Figure 10:
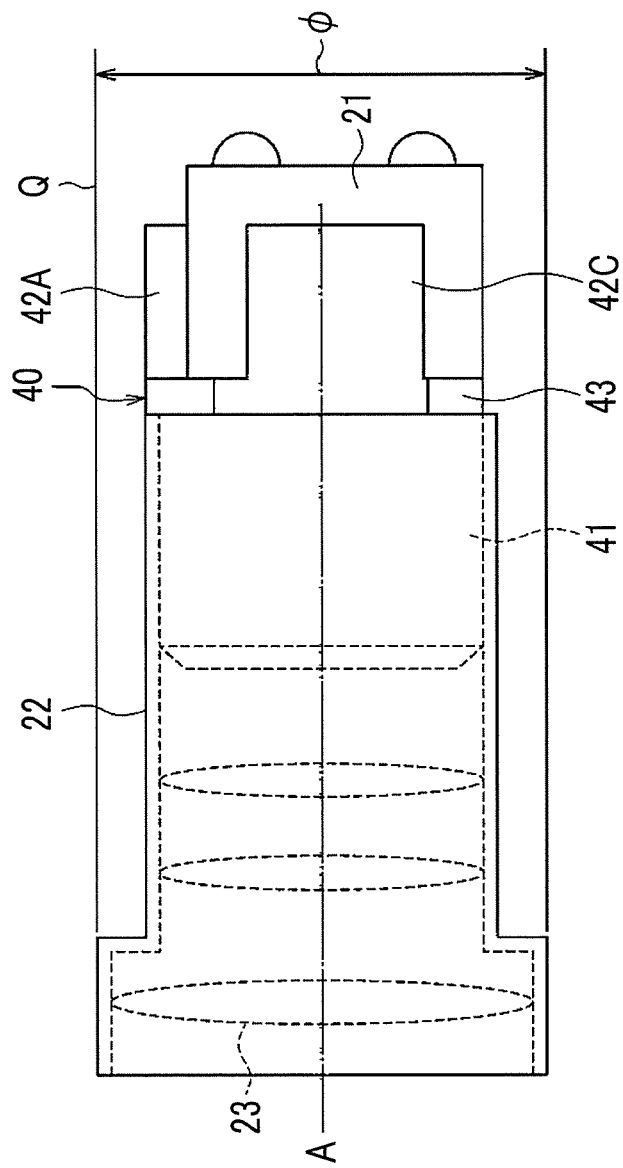
FIG. 10 is a side view illustrating a relationship between the sensor holder holding the image sensor and the external diameter dimension of a lens barrel.
Figure 11:
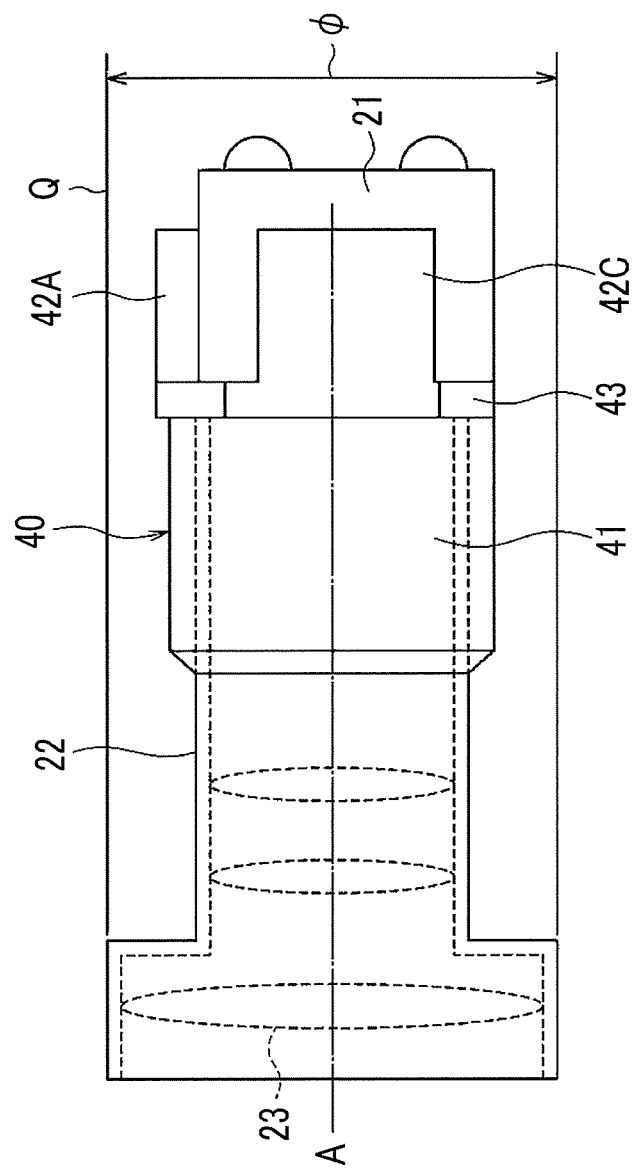
FIG. 11 is a side view illustrating a relationship between the sensor holder holding the image sensor and the external diameter dimension of the lens barrel.

FIGS. 10 and 11 are side views illustrating a relationship between the external diameter dimension of the sensor holder 40 holding the image sensor 21 and the external diameter dimension of the lens barrel 22. FIG. 10 illustrates an example in which the lens barrel 22 is fitted to the outside of the fitting part 41 of the sensor holder 40, and FIG. 11 illustrates an example in which the lens barrel 22 is fitted to the inside of the fitting part 41 of the sensor holder 40. In either case of FIGS. 10 and 11, as seen from the optical axis A of the imaging lens 23, a circumscribed circle of a portion with the largest diameter of the lens barrel 22 coincides with the circumscribed circle Q, illustrated in FIG. 7, of the image sensor 21 held by the sensor holder 40. In addition, the lens barrel 22 may be included inside the circumscribed circle Q. That is, in a case where the sensor holder 40 holding the image sensor 21 and the lens barrel 22 are projected on a plane orthogonal to the longitudinal direction of the insertion part 6, the lens barrel 22 may be located inside the circumscribed circle Q.

According to the configuration of the present embodiment described above, the image sensor 21 to be held by the sensor holder 40 is positioned and fixed in a state where the image sensor 21 is covered with the three wall parts 42A, 42B, and 42C that are configured integrally with the fitting part 41. The three wall parts 42A, 42B, and 42C are respectively independent, and the gap length in the first direction (X-axis direction) and the gap length in the second direction (Y-axis direction) between the adjacent wall parts of the three wall parts 42A, 42B, and 42C are equal to each other. For this reason, in a case where linear work is performed in the X-axis direction and the Y-axis direction without changing the height using the end mill of the same external diameter as the gap length, the gap between the adjacent wall parts of the three wall parts 42A, 42B, and 42C can be easily formed. In addition, the external diameter of the end mill is preferably 0.2 mm to 0.3 mm.

In addition, the height h of the three wall parts 42A, 42B, and 42C is selected to be in a range ($1.5d \leq h \leq 3d$) of 1.5 times to 3 times the gap length d between the adjacent wall parts. Although a machining tool in which the cutting edge length of the end mill is equal to or greater than the height h is used, there is a possibility that the end mill is distorted during the cutting work in a case where the cutting edge length is longer than the external diameter of the end mill. However, in the present embodiment, the end mill of the cutting edge length 1.5 times to 3 times the external diameter is used. Therefore, the easiness of machining by the end mill can be increased while guaranteeing the shape accuracy of the wall parts, the gap, and the like. As a result, the image pick-up device 20 comprising the sensor holder 40 with high manufacturability can be manufactured.

Additionally, the two wall parts 42A and 42B, which are orthogonal to each other, among the three wall parts 42A, 42B, and 42C that constitute the first wall portion 44 for causing the two side surfaces 21a and 21b, which are orthogonal to each other, among the four side surfaces 21a to 21d that constitute the outer peripheral surface of the image sensor 21, to abut against each other to position the image sensor 21 with respect to the sensor holder 40. For this reason, by causing the two side surfaces 21a and 21b of the image sensor 21 to abut against the first wall portion 44 in a case where alignment of the image sensor 21 with the sensor holder 40 is performed, the image sensor 21 can be easily positioned with high accuracy without requiring a special jig or advanced skills.

Additionally, the wall part 42C, which faces the wall part (wall part 42B) that constitutes the first wall portion 44, constitute the second wall portion 45 that faces the one side surface 21d of the four side surfaces 21a to 21d of the image sensor 21, and the gap is present between the image sensor 21 and the second wall portion 45. By filling this gap with the adhesive 46 to form the adhesive layer 47 between the image sensor 21 and the second wall portion 45, the image sensor 21 can be fixed to the sensor holder 40 in a state where the image sensor 21 is positioned with high accuracy.

Additionally, in a case where the sensor holder 40 holding the image sensor 21 is seen in the longitudinal direction (a direction of the optical axis A) of the insertion part 6, the three wall parts 42A, 42B, and 42C are located inside the circumscribed circle Q of the image sensor 21. Therefore, even in a case where the three wall parts 42A, 42B, and 42C are provided in the sensor holder 40, diameter reduction of the image pick-up device 20 can be maintained.

Additionally, height h of three wall parts 42A, 42B, and 42C is less than the thickness L1 of the image sensor 21 excluding the height of the connecting terminal 26, and the respective wall parts do not reach the position of an end part on the connecting terminals 26 side of the image sensor 21. For this reason, even in a case where there are protrusions, such as burrs, at the end part on the connecting terminals 26 side of the image sensor 21, the three wall parts 42A, 42B, and 42C do not interfere with the protrusions. Hence, the image sensor 21 can be accurately positioned.

Additionally, since the three wall parts 42A, 42B, and 42C extend to positions exceeding half (L1/2) of the thickness L1 of the image sensor 21, the adhesive layer 47 of sufficient area between the image sensor 21 and the wall part 42C (the second wall portion 45) can be provided. Therefore, the fixing strength of the image sensor 21 can be guaranteed.

Moreover, the diameter of the image pick-up device 20 can be minimized by causing the outer periphery of the portion with the largest external diameter among elements, such as the lens barrel 22 and the sensor holder 40, which constitute the image pick-up device 20, to coincide with the circumscribed circle Q of the image sensor 21 or by receiving the outer periphery inside the circumscribed circle Q.

In addition, the invention is not limited to the above embodiment, and can be appropriately modified, improved, or the like. For example, in the above embodiment, in a case where the three wall parts 42A, 42B, and 42C of the sensor holder 40 are cut and formed by the end mill, outer portions of the three wall parts 42A, 42B, and 42C are cut and removed (D cut). However, electronic components or the like may be disposed in a space where the D cut is performed. Additionally, the outer portions may be left without being cut and removed as long as the outer portions fall within the circumscribed circle Q of the image sensor 21.

Figure 12:
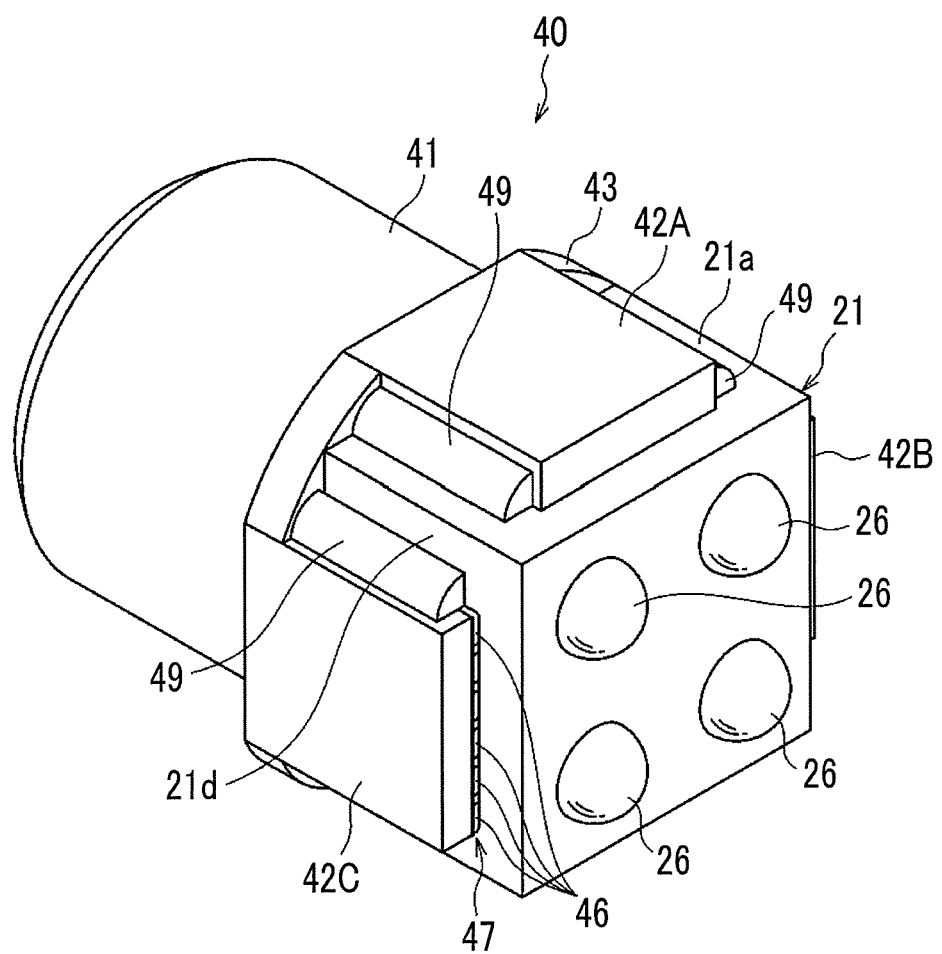
FIG. 12 is a perspective view of the proximal end side illustrating another state where the image sensor is held by the sensor holder.

Additionally, in the above embodiment, in order to fix the image sensor 21 to the sensor holder 40, as illustrated in FIG. 6, the adhesive 46 is filled into the gap between the wall part 42C of the sensor holder 40 and the side surface 21d of the image sensor 21 to form the adhesive layer 47. However, the adhesive may be further applied to other points. FIG. 12 is a perspective view of the proximal end side illustrating a state where the image sensor 21 is held by the sensor holder 40 even at points other than the adhesive layer 47. Additionally, FIG. 13 is a view of the sensor holder 40 holding the image sensor 21 as seen from the proximal end side in the state illustrated in FIG. 12.

Figure 13:
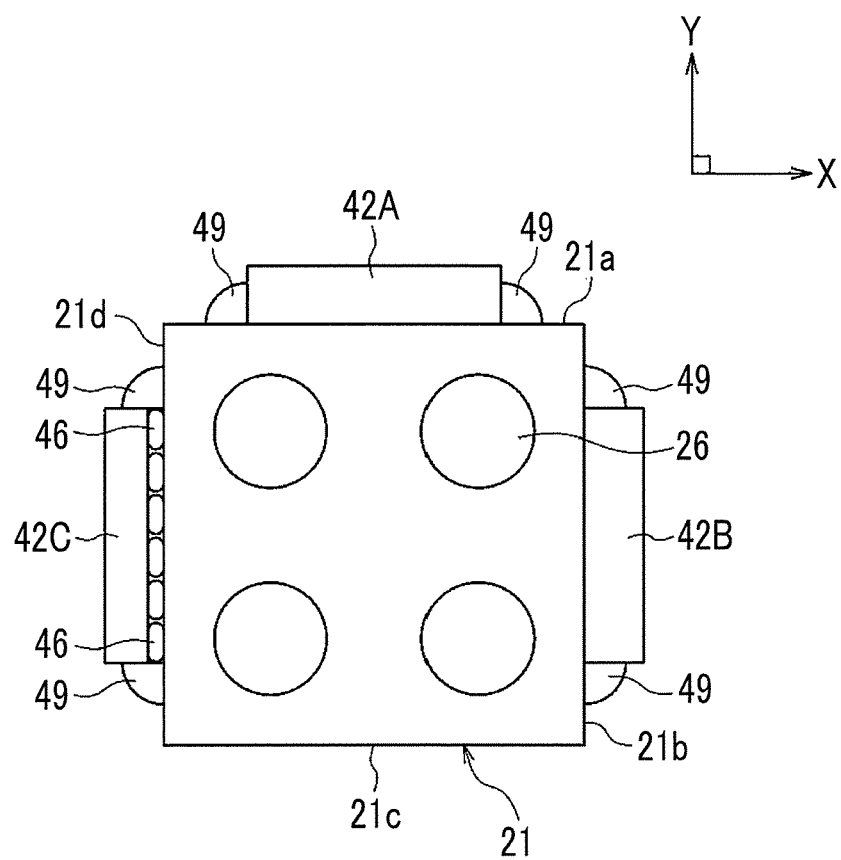
FIG. 13 is a view of the sensor holder holding the image sensor as seen from the proximal end side in the state illustrated in FIG. 12.

In an example illustrated in FIGS. 12 and 13, an adhesive 49 is applied in the longitudinal direction of the insertion part 6 between both end surfaces, in the X-axis direction, of the wall part 42A of the sensor holder 40, and the side surface 21a of the image sensor 21, and the adhesive 49 is applied in the longitudinal direction of the insertion part 6, between both end surfaces, in the Y-axis direction, of the two wall parts 42B and 42C that face the sensor holder 40, and the side surfaces 21b and 21d of the image sensor 21. The adhesive 49 may be the same adhesive as the adhesive 46 or may be a silicon-resin-based or epoxy-resin-based adhesive with high waterproofness.

As in the example illustrated in FIGS. 12 and 13, by applying the adhesive 49 to corner parts of respective spaces formed by respective end surfaces of the three wall parts 42A, 42B, and 42C of the sensor holder 40 and the outer peripheral surface of the image sensor 21 in addition to the adhesive layer 47 between the wall part 42C of the sensor holder 40 and the side surface 21d of the image sensor 21, the fixing strength of the image sensor 21 to the sensor holder 40 can be improved, and durability against bending stress or the like can be improved.

In addition, the same adhesive as the adhesive 49 may be applied in the X-axis direction illustrated in FIG. 13 also between the end part of the wall part 42A of the sensor holder 40 on the proximal end side in the longitudinal direction of the insertion part 6, and the side surface 21a of the image sensor 21. In addition, the same adhesive as the adhesive 49 may be applied in the Y-axis direction illustrated in FIG. 13 also between the respective end parts of the two facing wall parts 42B and 42C of the sensor holder 40 on the proximal end side in the longitudinal direction of the insertion part 6, and the side surfaces 21b and 21d of the image sensor 21. In this case, the fixing strength of the image sensor 21 to the sensor holder 40 can be further increased.

Additionally, in the above embodiment, the extending wall part 42 of the sensor holder 40 is constituted of the three wall parts 42A, 42B, and 42C. However, the extending wall part 42 may be made up of only the two wall parts 42A and 42B that are orthogonal to each other and provided for positioning the image sensor 21 with respect to the sensor holder 40. Additionally the extending wall part 42 may be constituted of four independent wall parts that respectively cover the four side surfaces that constitute the outer peripheral surface of the image sensor 21.

As described above, an endoscope disclosed in the present specification comprises an image pick-up device at a distal end part of an insertion part capable of being inserted into a body cavity. The image pick-up device includes a housing member that holds an imaging lens; a solid-state image pick-up element that photoelectrically converts imaging light incident on an image reception surface via the imaging lens and has a rectangular shape as an outer peripheral shape of the image reception surface; and a holding member that holds the solid-state image pick-up element in a state where the image reception surface intersects a longitudinal direction of the insertion part. The holding member has three independent wall parts that respectively cover three of four side surfaces that constitute an outer peripheral surface of the solid-state image pick-up element. On the plane orthogonal to the longitudinal direction of the insertion part, a gap length, in a first direction on a plane, between adjacent wall parts of the three wall parts and a gap length, in a second direction perpendicular to the first direction on the plane, between the adjacent wall parts are equal to each other, and a height of the three wall parts is 1.5 times to 3 times the gap length.

Additionally, the three wall parts include a first wall portion that abuts against the outer peripheral surface of the solid-state image pick-up element and is made up of two wall parts orthogonal to each other.

Additionally, the three wall parts include a second wall portion made up of one wall part that faces one of the four side surfaces of the solid-state image pick-up element, and the solid-state image pick-up element is fixed to the second wall portion by an adhesive.

Additionally, an adhesive layer including the adhesive is present between the solid-state image pick-up element and the second wall portion.

Additionally, the three wall parts are located inside a circumscribed circle of the solid-state image pick-up element in a case where the holding member holding the solid-state image pick-up element is seen in the longitudinal direction.

Additionally, the height of the three wall parts is less than a thickness of the solid-state image pick-up element.

Additionally, the height of the three wall parts is equal to or greater than half of the thickness of the solid-state image pick-up element.

Additionally, the housing member is located inside a circumscribed circle circumscribed on a projection outermost diameter end of the solid-state image pick-up element and the holding member in a case where the holding member holding the solid-state image pick-up element and the housing member are projected on the plane orthogonal to the longitudinal direction.

EXPLANATION OF REFERENCES

2: endoscope
6: insertion part
20: image pick-up device
21: image sensor (solid-state image pick-up element)
21a to 21d: side surface
22: lens barrel (housing member)
23: imaging lens
40: sensor holder (holding member)
41: fitting part
42: extending wall part
42A, 42B, 42C: wall part
44: first wall portion
45: second wall portion
46: adhesive
47: adhesive layer
49: adhesive
L1: thickness
h: height
Q: circumscribed circle

What is claimed is:

1. An endoscope comprising:
an image pick-up device at a distal end part of an insertion part capable of being inserted into a body cavity,
wherein the image pick-up device includes
a housing member that holds an imaging lens;
a solid-state image pick-up element that photoelectrically converts imaging light incident on an image reception surface via the imaging lens and has a rectangular shape as an outer peripheral shape of the image reception surface; and
a holding member that holds the solid-state image pick-up element in a state where the image reception surface intersects a longitudinal direction of the insertion part,
wherein the holding member has three independent wall parts that respectively cover three of four side surfaces that constitute an outer peripheral surface of the solid-state image pick-up element,
wherein, on a plane orthogonal to the longitudinal direction of the insertion part, a gap length, in a first direction on the plane, between adjacent wall parts of the three wall parts and a gap length, in a second direction perpendicular to the first direction on the plane, between the adjacent wall parts are equal to each other, and
wherein a height of the three wall parts is 1.5 times to 3 times the gap length, wherein the three wall parts are located inside a circumscribed circle of the solid-state image pick-up element in a case where the holding member holding the solid-state image pick-up element is seen in the longitudinal direction, two corners of each of the three wall parts are inscribed on the circumscribed circle in the case where the holding member holding the solid-state image pick-up element is seen in the longitudinal direction, and four peaks that constitute an outer periphery of the solid-state image pick-up element are inscribed on the circumscribed circle in the case where the holding member holding the solid-state image pick-up element is seen in the longitudinal direction.

2. The endoscope according to claim 1,
wherein the three wall parts include a first wall portion that abuts against the outer peripheral surface of the solid-state image pick-up element and is made up of two wall parts orthogonal to each other.

3. The endoscope according to claim 2,
wherein the three wall parts include a second wall portion made up of one wall part that faces one of the four side surfaces of the solid-state image pick-up element, and
wherein the solid-state image pick-up element is fixed to the second wall portion by an adhesive.

4. The endoscope according to claim 3,
wherein an adhesive layer including the adhesive is present between the solid-state image pick-up element and the second wall portion.

5. The endoscope according to claim 4,
wherein the height of the three wall parts is less than a thickness of the solid-state image pick-up element.

6. The endoscope according to claim 3,
wherein the height of the three wall parts is less than a thickness of the solid-state image pick-up element.

7. The endoscope according to claim 2,
wherein the height of the three wall parts is less than a thickness of the solid-state image pick-up element.

8. The endoscope according to claim 1,
wherein the three wall parts include a second wall portion made up of one wall part that faces one of the four side surfaces of the solid-state image pick-up element, and
wherein the solid-state image pick-up element is fixed to the second wall portion by an adhesive.

9. The endoscope according to claim 8,
wherein an adhesive layer including the adhesive is present between the solid-state image pick-up element and the second wall portion.

10. The endoscope according to claim 9,
wherein the height of the three wall parts is less than a thickness of the solid-state image pick-up element.

11. The endoscope according to claim 8,
wherein the height of the three wall parts is less than a thickness of the solid-state image pick-up element.

12. The endoscope according to claim 1,
wherein the height of the three wall parts is less than a thickness of the solid-state image pick-up element.

13. The endoscope according to claim 12,
wherein the height of the three wall parts is equal to or greater than half of the thickness of the solid-state image pick-up element.

14. The endoscope according to claim 1,
wherein the housing member is located inside a circumscribed circle circumscribed on a projection outermost diameter end of the solid-state image pick-up element and the holding member in a case where the holding member holding the solid-state image pick-up element and the housing member are projected on the plane orthogonal to the longitudinal direction.

15. An endoscope comprising:
an image pick-up device at a distal end part of an insertion part capable of being inserted into a body cavity,
wherein the image pick-up device includes
a lens barrel that holds an imaging lens;
a solid-state image pick-up element that photoelectrically converts imaging light incident on an image reception surface via the imaging lens and has a rectangular shape as an outer peripheral shape of the image reception surface; and
a holding member that holds the solid-state image pick-up element in a state where the image reception surface intersects a longitudinal direction axis of the insertion part,
wherein the holding member has a fitting part fitted to the lens barrel, and an extending wall part that extends in the longitudinal direction axis from the fitting part to cover at least a portion of the outer peripheral surface of the solid-state image pick-up element,
wherein the fitting part and the extending wall part are integrally configured,
wherein the extending wall part includes two wall parts that respectively cover two of four side surfaces that constitute the outer peripheral surface of the solid-state image pick-up element, and
wherein the two wall parts are located inside a circumscribed circle circumscribed on a projection outermost diameter end of the solid-state image pick-up element in a case where the holding member holding the solid-state image pick-up element is projected on a plane orthogonal to the longitudinal direction of the insertion part, two corners of each of the two wall parts are inscribed on the circumscribed circle the case where the holding member holding the solid-state image pick-up element is seen in the longitudinal direction, and four peaks that constitute an outer periphery of the solid-state image pick-up element are inscribed on the circumscribed circle in a case where the holding member holding the solid-state image pick-up element is projected on a plane orthogonal to the longitudinal direction.

16. The endoscope according to claim 15,
wherein the image pick-up device comprises a circuit board, and the solid-state image pick-up element is mounted on the circuit board.

17. The endoscope according to claim 16,
wherein the image pick-up device comprises a plurality of cables, and the plurality of cables are connected to the circuit board.

18. The endoscope according to claim 15,
wherein the solid-state image pick-up element comprises a plurality of terminals, and the plurality of terminals are disposed on a surface of the solid-state image pick-up element.

* * * * *